(12) United States Patent
Jina

(10) Patent No.: US 7,949,382 B2
(45) Date of Patent: May 24, 2011

(54) DEVICES, SYSTEMS, METHODS AND TOOLS FOR CONTINUOUS GLUCOSE MONITORING

(75) Inventor: Arvind N. Jina, San Jose, CA (US)

(73) Assignee: ArKal Medical, Inc., Fremont, CA (US)

( * ) Notice: Subject to any disclaimer, the term of this patent is extended or adjusted under 35 U.S.C. 154(b) by 0 days.

(21) Appl. No.: 12/844,710

(22) Filed: Jul. 27, 2010

(65) Prior Publication Data

US 2010/0292551 A1  Nov. 18, 2010

Related U.S. Application Data

(63) Continuation of application No. 11/277,731, filed on Mar. 28, 2006.

(60) Provisional application No. 60/666,775, filed on Mar. 29, 2005, provisional application No. 60/743,080, filed on Dec. 27, 2005.

(51) Int. Cl.
*A61B 5/05* (2006.01)
(52) U.S. Cl. .................. 600/347; 600/345; 600/365
(58) Field of Classification Search .......... 600/345–347, 600/365
See application file for complete search history.

(56) References Cited

U.S. PATENT DOCUMENTS

| | | | |
|---|---|---|---|
| 3,964,482 A | 6/1976 | Gerstel et al. | |
| 4,018,938 A | 4/1977 | Feder et al. | |
| 4,071,020 A | 1/1978 | Pugliese | |
| 4,165,395 A | 8/1979 | Chang | |
| 4,320,758 A | 3/1982 | Eckenhoff et al. | |
| 4,523,807 A | 6/1985 | Suzuki | |
| 4,821,733 A | 4/1989 | Peck | |
| 4,846,950 A * | 7/1989 | Yao et al. ................ | 204/229.2 |

(Continued)

FOREIGN PATENT DOCUMENTS

WO    WO86/07632 A1    12/1986

(Continued)

OTHER PUBLICATIONS

Boutelle et al; "An amperometric enzyme electrode for monitoring brain glucose in the freely moving rat." Neurosci Lett. 1986; 72(3):283-8.

(Continued)

*Primary Examiner* — Charles A Marmor, II
*Assistant Examiner* — Michael D'Angelo
(74) *Attorney, Agent, or Firm* — Shay Glenn LLP

(57) ABSTRACT

One aspect of the invention provides a glucose monitor having a plurality of tissue piercing elements, each tissue piercing element having a distal opening, a proximal opening and interior space extending between the distal and proximal openings; a sensing area in fluid communication with the proximal openings of the tissue piercing elements; sensing fluid extending from the sensing area into substantially the entire interior space of the tissue piercing elements; and a glucose sensor adapted to detect a concentration of glucose in the sensing fluid within the sensing area. Another aspect of the invention provides a method of in vivo monitoring of an individual's interstitial fluid glucose concentration including the following steps: inserting distal ends of a plurality of tissue piercing elements through a stratum corneum area of the individual's skin, the tissue piercing elements each having a distal opening, a proximal opening, an interior space extending between the distal and proximal openings, and a sensing fluid filling substantially the entire interior space; and sensing a glucose concentration of the sensing fluid.

16 Claims, 7 Drawing Sheets

U.S. PATENT DOCUMENTS

| | | |
|---|---|---|
| 5,076,273 A | 12/1991 | Schoendorfer et al. |
| 5,096,669 A | 3/1992 | Lauks et al. |
| 5,112,455 A | 5/1992 | Cozzette et al. |
| 5,208,147 A | 5/1993 | Kagenow et al. |
| 5,258,107 A | 11/1993 | Yoshida et al. |
| 5,384,028 A | 1/1995 | Ito |
| 5,389,954 A | 2/1995 | Inaba et al. |
| 5,438,984 A | 8/1995 | Schoendorfer |
| 5,447,440 A | 9/1995 | Davis et al. |
| 5,457,041 A | 10/1995 | Ginaven et al. |
| 5,543,108 A | 8/1996 | Bacher et al. |
| 5,569,272 A | 10/1996 | Reed et al. |
| 5,582,184 A | 12/1996 | Erickson et al. |
| 5,640,954 A | 6/1997 | Pfeiffer et al. |
| 5,641,504 A | 6/1997 | Lee et al. |
| 5,676,850 A | 10/1997 | Reed et al. |
| 5,722,397 A | 3/1998 | Eppstein |
| 5,735,273 A | 4/1998 | Kurnik et al. |
| 5,747,666 A | 5/1998 | Willis |
| 5,817,012 A | 10/1998 | Schoendorfer |
| 5,821,399 A | 10/1998 | Zelin et al. |
| 5,885,211 A | 3/1999 | Eppstein et al. |
| 5,899,856 A | 5/1999 | Schoendorfer et al. |
| 5,928,207 A | 7/1999 | Pisano et al. |
| 5,989,409 A | 11/1999 | Kurnik et al. |
| 6,013,029 A | 1/2000 | Korf et al. |
| 6,050,988 A | 4/2000 | Zuck |
| 6,093,520 A | 7/2000 | Vladimirsky et al. |
| 6,106,751 A | 8/2000 | Talbot et al. |
| 6,132,755 A | 10/2000 | Eicher et al. |
| 6,139,718 A | 10/2000 | Kurnik et al. |
| 6,144,869 A | 11/2000 | Berner et al. |
| 6,190,315 B1 | 2/2001 | Kost et al. |
| 6,219,574 B1 | 4/2001 | Cormier et al. |
| 6,223,591 B1 | 5/2001 | Nakano |
| 6,233,471 B1 | 5/2001 | Berner et al. |
| 6,256,533 B1 | 7/2001 | Yuzhakov et al. |
| 6,275,717 B1 | 8/2001 | Gross et al. |
| 6,287,438 B1 | 9/2001 | Knoll |
| 6,322,808 B1 | 11/2001 | Trautman et al. |
| 6,334,856 B1 | 1/2002 | Allen et al. |
| 6,379,324 B1 | 4/2002 | Gartstein et al. |
| 6,398,562 B1 | 6/2002 | Butler et al. |
| 6,406,638 B1 | 6/2002 | Stoeber et al. |
| 6,434,409 B1 | 8/2002 | Pfeiffer et al. |
| 6,463,312 B1* | 10/2002 | Bergveld et al. ............... 600/345 |
| 6,503,231 B1 | 1/2003 | Prausnitz et al. |
| 6,533,949 B1 | 3/2003 | Yeshurun et al. |
| 6,537,264 B1 | 3/2003 | Cormier et al. |
| 6,558,361 B1 | 5/2003 | Yeshurun |
| 6,565,509 B1* | 5/2003 | Say et al. ...................... 600/365 |
| 6,565,532 B1 | 5/2003 | Yuzhakov et al. |
| 6,591,126 B2 | 7/2003 | Roeper et al. |
| 6,602,678 B2 | 8/2003 | Kwon et al. |
| 6,603,987 B2 | 8/2003 | Whitson |
| 6,611,707 B1 | 8/2003 | Prausnitz et al. |
| 6,652,478 B1 | 11/2003 | Gartstein et al. |
| 6,689,100 B2 | 2/2004 | Connelly et al. |
| 6,749,792 B2 | 6/2004 | Olson |
| 6,767,341 B2 | 7/2004 | Cho |
| 6,771,995 B2 | 8/2004 | Kurnik et al. |
| 6,816,742 B2 | 11/2004 | Kim et al. |
| 6,835,184 B1 | 12/2004 | Sage et al. |
| RE38,681 E | 1/2005 | Kurnik et al. |
| 6,875,613 B2 | 4/2005 | Shartle et al. |
| 6,881,203 B2 | 4/2005 | Delmore et al. |
| 6,885,883 B2 | 4/2005 | Parris et al. |
| 6,902,905 B2 | 6/2005 | Burson et al. |
| 6,908,453 B2 | 6/2005 | Fleming et al. |
| RE38,775 E | 8/2005 | Kurnik et al. |
| 6,945,964 B2 | 9/2005 | Ross et al. |
| 6,962,772 B2 | 11/2005 | Liu et al. |
| 6,990,367 B2 | 1/2006 | Kiser et al. |
| 7,025,774 B2 | 4/2006 | Freeman et al. |
| 7,060,059 B2 | 6/2006 | Keith et al. |
| 7,066,884 B2 | 6/2006 | Custer et al. |
| 7,076,987 B2 | 7/2006 | Martin et al. |
| 7,087,035 B2 | 8/2006 | Trautman et al. |
| 7,131,960 B2 | 11/2006 | Trautman et al. |
| 7,184,826 B2 | 2/2007 | Cormier et al. |
| 7,276,027 B2* | 10/2007 | Haar et al. ...................... 600/309 |
| 7,344,499 B1 | 3/2008 | Prausnitz et al. |
| 7,361,307 B2 | 4/2008 | Shartle et al. |
| 2002/0020688 A1 | 2/2002 | Sherman et al. |
| 2002/0045859 A1 | 4/2002 | Gartstein et al. |
| 2002/0133129 A1 | 9/2002 | Arias et al. |
| 2002/0169394 A1 | 11/2002 | Eppstein et al. |
| 2002/0177858 A1 | 11/2002 | Sherman et al. |
| 2002/0188185 A1 | 12/2002 | Sohrab |
| 2003/0135166 A1 | 7/2003 | Gonnelli |
| 2003/0135201 A1 | 7/2003 | Gonnelli |
| 2003/0143113 A2 | 7/2003 | Yuzhakov et al. |
| 2003/0143746 A1 | 7/2003 | Sage |
| 2003/0153820 A1 | 8/2003 | Berner et al. |
| 2003/0153900 A1 | 8/2003 | Aceti et al. |
| 2003/0208167 A1* | 11/2003 | Prausnitz et al. ............. 604/272 |
| 2004/0019331 A1* | 1/2004 | Yeshurun ...................... 604/173 |
| 2004/0044308 A1 | 3/2004 | Naimark et al. |
| 2004/0096959 A1 | 5/2004 | Stiene et al. |
| 2004/0106904 A1 | 6/2004 | Gonnelli et al. |
| 2004/0164454 A1 | 8/2004 | Gartstein et al. |
| 2004/0171980 A1 | 9/2004 | Mitragotri et al. |
| 2004/0186419 A1 | 9/2004 | Cho |
| 2004/0200734 A1 | 10/2004 | Co et al. |
| 2004/0236268 A1 | 11/2004 | Mitragotri et al. |
| 2004/0267205 A1 | 12/2004 | Stemme et al. |
| 2005/0027179 A1 | 2/2005 | Berner et al. |
| 2005/0038332 A1 | 2/2005 | Saidara et al. |
| 2005/0064528 A1 | 3/2005 | Kwon et al. |
| 2005/0124020 A1 | 6/2005 | Lee et al. |
| 2005/0130292 A1 | 6/2005 | Ahn et al. |
| 2005/0137536 A1* | 6/2005 | Gonnelli ....................... 604/264 |
| 2005/0171480 A1 | 8/2005 | Mukerjee et al. |
| 2005/0215872 A1 | 9/2005 | Berner et al. |
| 2005/0261606 A1 | 11/2005 | Sohrab |
| 2005/0261631 A1 | 11/2005 | Clarke et al. |
| 2005/0265914 A1 | 12/2005 | Gu et al. |
| 2006/0004272 A1 | 1/2006 | Shah et al. |
| 2006/0025717 A1 | 2/2006 | Zimmermann et al. |
| 2006/0047242 A1* | 3/2006 | Laurent et al. .................. 604/46 |
| 2006/0054936 A1 | 3/2006 | Lieber et al. |
| 2006/0058602 A1 | 3/2006 | Kwiatkowski et al. |
| 2006/0211933 A1* | 9/2006 | Zimmermann et al. ...... 600/352 |
| 2006/0219576 A1 | 10/2006 | Jina |
| 2006/0228723 A1 | 10/2006 | Bradley et al. |
| 2006/0258920 A1 | 11/2006 | Burd et al. |
| 2007/0004989 A1 | 1/2007 | Dhillon |
| 2007/0066934 A1 | 3/2007 | Etheredge et al. |
| 2008/0058726 A1 | 3/2008 | Jina et al. |
| 2008/0154107 A1 | 6/2008 | Jina |
| 2008/0234562 A1 | 9/2008 | Jina |
| 2008/0312518 A1 | 12/2008 | Jina et al. |
| 2009/0099427 A1 | 4/2009 | Jina et al. |
| 2009/0131778 A1 | 5/2009 | Jina et al. |
| 2010/0049021 A1 | 2/2010 | Jina et al. |

FOREIGN PATENT DOCUMENTS

| | | |
|---|---|---|
| WO | WO99/64580 A1 | 12/1999 |
| WO | WO03/056033 A1 | 7/2003 |
| WO | WO2005/060621 A2 | 7/2005 |
| WO | WO2006/105146 A2 | 10/2006 |

OTHER PUBLICATIONS

Cass et al; "Ferrocene-mediated enzyme electrode for amperometric determination of glucose." Anal Chem. 1984; 56(4):667-71.

Chandrasekaran et al; "Surface Micromachined Metallic Microneedles." J. Microelectromechan. Syst. 2003; 12:281-288.

Chuang et al.; Clinical evaluation of a continuous minimally invasive glucose flux sensor placed over ultrasonically permeated skin; Diabetes Technology & Therapeutics; vol. 6; No. 1; pp. 21-30; 2004.

Clague, David; Simulation-aided design of microfluidic devices; Lawrence Livermore National Laboratory; pp. 4-11; Dec. 2001.

Clark et al; "Electrode systems for continuous monitoring in cardiovascular surgery". Ann N Y Acad Sci. 1962; 102:29-45.

Gardeniers et al; "Silicon micromachined hollow microneedles for transdermal liquid transfer." Presented at MEMS 2002 IEEE International Conference, 15th IEEE International Conference on Micro Electro Mechanical Systems, Las Vegas, NV (Cat. No. 02CH37266) Technical Digest. 2002; pp. 141-144.

Griss et al; "Novel, side opened out-of-plane microneedles for microfluidic transdermal interfacing." Presented at MEMS 2002 IEEE International Conference, 15th IEEE International Conference on Micro Electro Mechanical Systems, Las Vegas, NV. (Cat. No. 02CH37266) Technical Digest. 2002; pp. 467-470.

Henry et al; "Microfabricated microneedles: a novel approach to transdermal drug delivery." J. Pharm. Sci. 1998; 87:922-925.

Kuo et al.; A novel polymer microneedle arrays and PDMS micromolding technique; Tamkang Journal of Science and Engineering; vol. 7; No. 2; pp. 95-98; 2004.

Lagally et al. Fully integrated PCR capillary electrophoresis microsystem for DNA analysis. Lab Chip 1. 2001:102-107.

Liu et al; "Electrophoresis separation in open microchannels. A method for coupling electrophoresis with MALDI-MS." Anal. Chem. 2001; 73:2147-2151.

Smart et al; "The use of silicon microfabrication technology in painless blood glucose monitoring," Diabetes Technol. Therapeutics. 2000; 2(4):549-559.

Szita et al; An actuation coupling system for a fast and low volume micropipetting device with integrated sensors. Presented at Actuator 2000, 7th Internat'l Conf. on New Actuators and Internat'l Exhibit. on Smart Actuators and Drive Systems. Conf. Proc. Messe Bremen GMBH, Bremen, Germany. 2000; pp. 228-231.

Updike et al; "The enzyme electrode." Nature. 1967; 214(92):986-8.

Visuri et al; "Microfluidic tools for biological sample preparation." Presented at 2nd Annual International IEEE-EMBS Special Topic Conference on Microtechnologies in Medicine and Biology. Proceedings (Cat. No. 02EX578). IEEE, Piscataway, N.J. USA. 2002; pp. 556-559.

* cited by examiner

DEVICES, SYSTEMS, METHODS AND TOOLS FOR CONTINUOUS GLUCOSE MONITORING

CROSS REFERENCE TO RELATED APPLICATIONS

This application is a continuation of application Ser. No. 11/277,731, entitled, "DEVICES, SYSTEMS, METHODS AND TOOLS FOR CONTINUOUS GLUCOSE MONITORING" filed on Mar. 28, 2006 which claims the benefit of U.S. Provisional Application No. 60/666,775, filed Mar. 29, 2005, and U.S. Provisional Application No. 60/743,080, filed Dec. 27, 2005, which are incorporated herein by reference in their entirety.

BACKGROUND OF THE INVENTION

The invention relates to systems, devices, and tools, and the use of such systems, devices and tools for monitoring blood glucose levels in a person having diabetes. More specifically, the invention relates to systems, devices, and tools and the use of such systems, devices and tools for monitoring blood glucose level continuously, or substantially continuously.

Diabetes is a chronic, life-threatening disease for which there is no known cure. It is a syndrome characterized by hyperglycemia and relative insulin deficiency. Diabetes affects more than 120 million people world wide, and is projected to affect more than 220 million people by the year 2020. It is estimated that 1 in 3 children today will develop diabetes sometime during their lifetime. Diabetes is usually irreversible, and can lead to a variety of severe health complications, including coronary artery disease, peripheral vascular disease, blindness and stroke. The Center for Disease Control (CDC) has reported that there is a strong association between being overweight, obesity, diabetes, high blood pressure, high cholesterol, asthma and arthritis. Individuals with a body mass index of 40 or higher are more than 7 times more likely to be diagnosed with diabetes.

There are two main types of diabetes, Type I diabetes (insulin-dependent diabetes mellitus) and Type II diabetes (non-insulin-dependent diabetes mellitus). Varying degrees of insulin secretory failure may be present in both forms of diabetes. In some instances, diabetes is also characterized by insulin resistance. Insulin is the key hormone used in the storage and release of energy from food.

As food is digested, carbohydrates are converted to glucose and glucose is absorbed into the blood stream primarily in the intestines. Excess glucose in the blood, e.g. following a meal, stimulates insulin secretion, which promotes entry of glucose into the cells, which controls the rate of metabolism of most carbohydrates.

Insulin secretion functions to control the level of blood glucose both during fasting and after a meal, to keep the glucose levels at an optimum level. In a normal person blood glucose levels are between 80 and 90 mg/dL of blood during fasting and between 120 to 140 mg/dL during the first hour or so following a meal. For a person with diabetes, the insulin response does not function properly (either due to inadequate levels of insulin production or insulin resistance), resulting in blood glucose levels below 80 mg/dL during fasting and well above 140 mg/dL after a meal.

Currently, persons suffering from diabetes have limited options for treatment, including taking insulin orally or by injection. In some instances, controlling weight and diet can impact the amount of insulin required, particularly for non-insulin dependent diabetics. Monitoring blood glucose levels is an important process that is used to help diabetics maintain blood glucose levels as near as normal as possible throughout the day.

The blood glucose self-monitoring market is the largest self-test market for medical diagnostic products in the world, with a size of approximately $3 billion in the United States and $5.0 billion worldwide. It is estimated that the worldwide blood glucose self-monitoring market will amount to $8.0 billion by 2006. Failure to manage the disease properly has dire consequences for diabetics. The direct and indirect costs of diabetes exceed $130 billion annually in the United States—about 20% of all healthcare costs.

There are two main types of blood glucose monitoring systems used by patients: single point or non-continuous and continuous. Non-continuous systems consist of meters and tests strips and require blood samples to be drawn from fingertips or alternate sites, such as forearms and legs (e.g. OneTouch® Ultra by LifeScan, Inc., Milpitas, Calif., a Johnson & Johnson company). These systems rely on lancing and manipulation of the fingers or alternate blood draw sites, which can be extremely painful and inconvenient, particularly for children.

Continuous monitoring sensors are generally implanted subcutaneously and measure glucose levels in the interstitial fluid at various periods throughout the day, providing data that shows trends in glucose measurements over a short period of time. These sensors are painful during insertion and usually require the assistance of a health care professional. Further, these sensors are intended for use during only a short duration (e.g., monitoring for a matter of days to determine a blood sugar pattern). Subcutaneously implanted sensors also frequently lead to infection and immune response complications. Another major drawback of currently available continuous monitoring devices is that they require frequent, often daily, calibration using blood glucose results that must be obtained from painful finger-sticks using traditional meters and test strips. This calibration, and re-calibration, is required to maintain sensor accuracy and sensitivity, but it can be cumbersome as well as painful.

At this time, there are four products approved by the FDA for continuous glucose monitoring, none of which are presently approved as substitutes for current glucose self-monitoring devices. Medtronic (www.medtronic.com) has two continuous glucose monitoring products approved for sale: Guardian® RT Real-Time Glucose Monitoring System and CGMS ® System. Each product includes an implantable sensor that measures and stores glucose values for a period of up to three days. One product is a physician product. The sensor is required to be implanted by a physician, and the results of the data aggregated by the system can only be accessed by the physician, who must extract the sensor and download the results to a personal computer for viewing using customized software. The other product is a consumer product, which permits the user to download results to a personal computer using customized software.

A third product approved for continuous glucose monitoring is the Glucowatch® developed by Cygnus Inc., which is worn on the wrist like a watch and can take glucose readings every ten to twenty minutes for up to twelve hours at a time. It requires a warm up time of 2 to 3 hours and replacement of the sensor pads every 12 hours. Temperature and perspiration are also known to affect its accuracy. The fourth approved product is a subcutaneously implantable glucose sensor developed by Dexcom, San Diego, Calif. (www.dexcom.com). All of the approved devices are known to require daily, often frequent, calibrations with blood glucose values which the patient must obtain using conventional finger stick blood glucose monitors.

SUMMARY OF THE INVENTION

The invention is a novel continuous glucose monitor that may be periodically calibrated without using finger sticks or other invasive calibration techniques and measures glucose without extracting any interstitial fluid (or any other fluid) from the user. The continuous glucose monitor may be configured to be self-calibrating.

One aspect of the invention provides a glucose monitor with a plurality of tissue piercing elements, each tissue piercing element having a distal opening, a proximal opening and interior space extending between the distal and proximal openings; a sensing area in fluid communication with the proximal openings of the tissue piercing elements; sensing fluid extending from the sensing area into substantially the entire interior space of the tissue piercing elements; and a glucose sensor adapted to detect a concentration of glucose in the sensing fluid within the sensing area. This arrangement permits interstitial fluid glucose to diffuse from the interstitial fluid into the sensing area without extracting interstitial fluid through the distal openings of the piercing elements into the interior space. In some embodiments, the glucose monitor has a removable cover extending over the distal openings of the tissue piercing elements.

In some embodiments, the glucose monitor has a display adapted to display a glucose concentration sensed by the sensor. The display may be disposed within a housing separate from the sensor, with the glucose monitor further including a communicator adapted to wirelessly communicate sensor information from the sensor to the display.

In some embodiments, the glucose monitor includes a sensing fluid reservoir and a pump adapted to move sensing fluid out of the sensing fluid reservoir into the sensing area. Such embodiments may have a manual actuator and may have a waste reservoir adapted to receive sensing fluid from the sensing area. In some such embodiments, the glucose monitor may have a housing with a first part and a second part, the first part of the housing being adapted to support the tissue piercing elements, the sensing fluid reservoir, the sensing area, and at least part of the sensor, the second part of the housing having an electrical connection to the at least part of the sensor in the first part of the housing, with the housing further including a connector adapted to connect and disconnect the first part of the housing from the second part of the housing. In some embodiments, the first part of the housing is further adapted to support the pump and optionally the waste reservoir. Some embodiments have a communicator supported by the second part of the housing and adapted to communicate sensor information to a display.

In some embodiments, the sensing fluid in the sensing fluid reservoir has a glucose concentration of between about 0 mg/dl and about 400 mg/dl. The sensing fluid may also contain buffers, preservatives or other materials in addition to the glucose. In yet other embodiments, the glucose monitor has an adhesive element adjacent the tissue piercing elements and adapted to attach to a user's skin. The glucose sensor, tissue piercing elements and sensing area may be further adapted to detect a concentration of glucose in the sensing fluid within the sensing area without extracting interstitial fluid through the distal openings into the interior space.

Another aspect of the invention provides a method of in vivo monitoring of an individual's interstitial fluid glucose concentration including the following steps: inserting distal ends of a plurality of tissue piercing elements through a stratum corneum area of the individual's skin, the tissue piercing elements each having a distal opening, a proximal opening, an interior space extending between the distal and proximal openings, and a sensing fluid filling substantially the entire interior space; and sensing a glucose concentration of the sensing fluid. This method permits interstitial fluid glucose to diffuse from the interstitial fluid into the sensing area without extracting interstitial fluid through the distal openings of the piercing elements into the interior space. Some embodiments include the step of removing a cover from the distal openings of the tissue piercing elements prior to the inserting step. Some embodiments include the step of displaying glucose concentration information remote from the stratum corneum area of the individual's skin. The method may also include the step of wirelessly communicating glucose concentration information to a display.

In some embodiments, the sensing step is performed by a sensor in fluid communication with a sensing area and the interior spaces of the tissue piercing elements, and the method further includes the step of calibrating the sensor by moving sensing fluid into the sensing area, such as by using a pump. The method may also include the step of moving sensing fluid out of the sensing area as sensing fluid is moved into the sensing area. The sensing fluid may have a glucose concentration of between about 0 mg/dl and about 400 mg/dl.

In embodiments in which the step of moving sensing fluid includes the steps of moving sensing fluid from a sensing fluid reservoir, the sensing fluid reservoir, sensing area, tissue piercing elements and at least part of the sensor may be supported by a first part of a housing, and the method further includes the step of attaching the first part of the housing to a second part of the housing prior to the inserting step, with the second part of the housing having an electrical connection to the at least part of the sensor in the first part of the housing. The method may also include the step of separating the second part of the housing from the first part of the housing after the sensing step.

In some embodiments, the method includes the step of attaching the tissue piercing elements to the individual with adhesive. In other embodiments, the method includes the step of permitting glucose to diffuse from interstitial fluid of the individual through the distal openings into the interior space.

Another embodiment of the invention includes a glucose monitor comprising a plurality of tissue piercing elements, each tissue piercing element comprising a distal opening, a proximal opening and an interior space extending between the distal and proximal openings; a sensing area in continuous fluid communication with the proximal openings of the tissue piercing elements; sensing fluid extending from the sensing area into substantially the entire interior space of the tissue piercing elements; and a glucose sensor adapted to continuously detect a concentration of glucose in the sensing fluid within the sensing area further adapted to be self-calibrating.

Other embodiments of the invention will be apparent from the specification and drawings.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention provides a significant advance in biosensor and glucose monitoring technology: portable, virtually non-invasive, self-calibrating, integrated and non-implanted sensors which continuously indicate the user's blood glucose concentration, enabling swift corrective action to be taken by the patient. The sensor and monitor of this invention may be used to measure other analytes as well, such as electrolytes like sodium or potassium ions. As will be appreciated by persons of skill in the art, the glucose sensor can be any suitable sensor including, for example, an electrochemical sensor an optical sensor.

Figure 1:
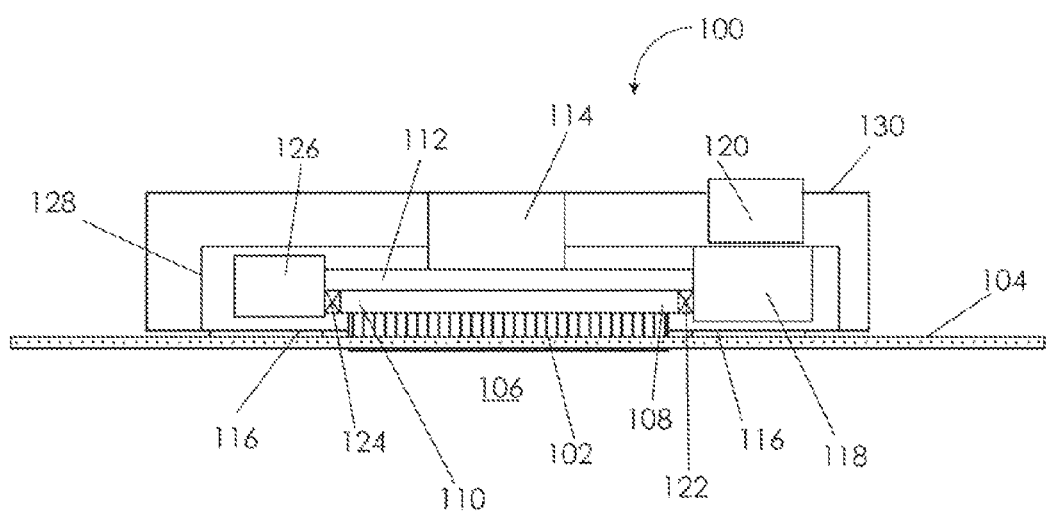
FIG. 1 is a cross-sectional schematic view of a glucose monitoring device according to one embodiment of the invention in place on a user's skin.

FIG. 1 shows a schematic cross-section of one embodiment of the invention in use. The glucose monitor 100 has an array of unique hollow microneedles 102 or other tissue piercing elements extending through the stratum corneum 104 of a user into the interstitial fluid 106 beneath the stratum corneum. Suitable microneedle arrays include those described in Stoeber et al. U.S. Pat. No. 6,406,638; US Patent Appl. Publ. No. 2005/0171480; and US Patent Appl. Publ. No. 2006/0025717. The needles in array 102 are hollow and have open distal ends, and their interiors communicate with a sensing area 110 within a sensor channel 108. Sensing area 110 is therefore in fluid communication with interstitial fluid 106 through microneedle array 102. In this embodiment, sensing area 110 and the microneedles 102 are pre-filled with sensing fluid prior to the first use of the device. Thus, when the device is applied to the user's skin and the microneedles pierce the stratum corneum of the skin, there is substantially no net fluid transfer from the interstitial fluid into the microneedles. Rather, glucose diffuses from the interstitial fluid into the sensing fluid within the needles, as described below.

Disposed above and in fluid communication with sensor channel 108 is a glucose sensor 112. In some embodiments, glucose sensor is an electrochemical glucose sensor that generates an electrical signal (current, voltage or charge) whose value depends on the concentration of glucose in the fluid within sensing area 110. Details of the operation of glucose sensor 112 are discussed in more detail below.

Sensor electronics element 114 receives the voltage signal from sensor 112. In some embodiments, sensor electronics element 114 uses the sensed signal to compute a glucose concentration and display it. In other embodiments, sensor electronics element 114 transmits the sensed signal, or information derived from the sensed signal, to a remote device, such as through wireless communication. Glucose monitor 100 is held in place on the skin 104 by one or more adhesive pads 116.

Glucose monitor 100 has a novel built-in sensor calibration system. A reservoir 118 containing a sensing fluid having, e.g., a glucose concentration between about 0 and about 400 mg/dl. In some embodiments, the glucose concentration in the sensing fluid is selected to be below the glucose sensing range of the sensor. The sensing fluid may also contain buffers, preservatives or other components in addition to the glucose. Upon actuation of a pump manually or automatically, plunger or other actuator 120, sensing fluid is forced from reservoir 118 through a check valve 122 (such as a flap valve) into sensing channel 108. Any sensing fluid within channel 108 is forced through a second check valve 124 (e.g., a flap valve) into a waste reservoir 126. Check valves or similar gating systems are used to prevent contamination. Because the fresh sensing fluid has a known glucose concentration, sensor 112 can be calibrated at this value to set a base line. After calibration, the sensing fluid in channel 108 remains stationary, and glucose from the interstitial fluid 106 diffuses through microneedles 102 into the sensing area 110. Changes in the glucose concentration from over time reflect differences between the calibration glucose concentration of the sensing fluid in the reservoir 118 and the glucose concentration of the interstitial fluid which can be correlated with the actual blood glucose concentration of the user using proprietary algorithms. Because of possible degradation of the sensor or loss of sensor sensitivity over time, the device may be periodically recalibrated by operating actuator 120 manually or automatically to send fresh sensing fluid from reservoir 118 into sensing area 110.

In some embodiments, microneedle array 102, reservoirs 118 and 126, channel 108, sensor 112 and adhesive pads 116 are contained within a support structure (such as a housing 128) separate from electronics element 114 and actuator 120, which are supported within their own housing 130. This arrangement permits the sensor, sensing fluid and microneedles to be discarded after a period of use (e.g., when reservoir 118 is depleted) while enabling the electronics and actuator to be reused. A flexible covering (made, e.g., of polyester or other plastic-like material) may surround and support the disposable components. In particular, the interface between actuator 120 and reservoir 118 must permit actuator 120 to move sensing fluid out of reservoir 118, such as by deforming a wall of the reservoir. In these embodiments, housings 128 and 130 may have a mechanical connection, such as a snap or interference fit.

Figure 2:
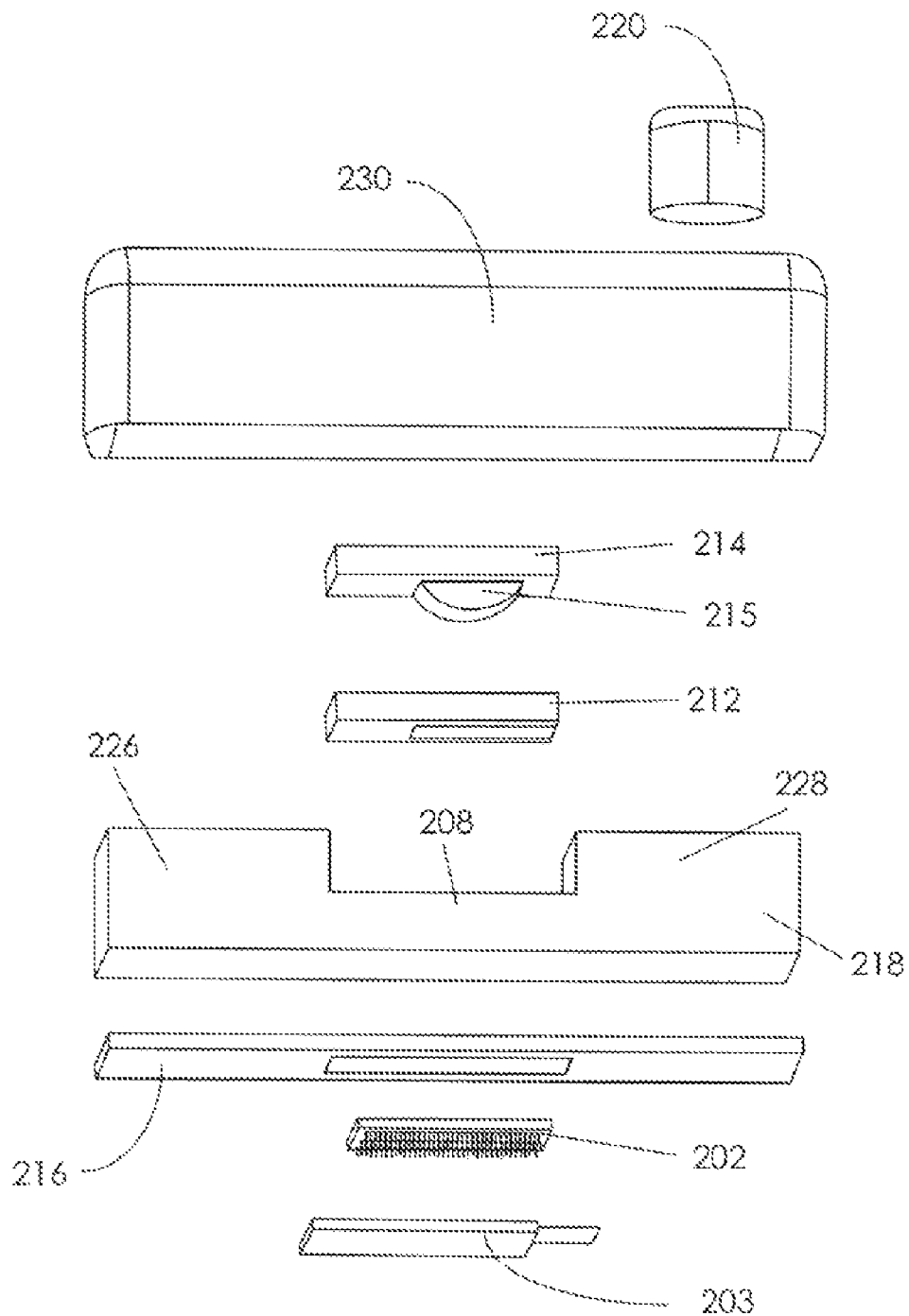
FIG. 2 shows an exploded view of a glucose monitoring device according to another embodiment of the invention.

FIG. 2 shows an exploded view of another embodiment of the invention. This figure shows a removable seal 203 covering the sharp distal ends of microneedles 202 and attached, e.g., by adhesive. Seal 203 maintains the sensing fluid within the microneedles and sensing area prior to use and is removed prior to placing the glucose monitor 200 on the skin using adhesive pressure seal 216. In this embodiment, microneedles 202, sensing fluid and waste reservoirs 218 and 226, sensing microchannel 208 and electrochemical glucose sensor 212 are contained within and/or supported by a housing 228 which forms the disposable portion of the device. A second housing 230 supports an electronics board 214 (containing, e.g., processing circuitry, a power source, transmission circuitry, etc.) and an actuator 220 that can be used to move sensing fluid out of reservoir 218, through microchannel 208 into waste reservoir 226. Electrical contacts 215 extend from electronics board 214 to make contact with corresponding electrodes in glucose sensor 212 when the device is assembled.

The following is a description of glucose sensors that may be used with the glucose monitors of this invention. In 1962 Clark and Lyons proposed the first enzyme electrode (that was implemented later by Updike and Hicks) to determine glucose concentration in a sample by combining the specificity of a biological system with the simplicity and sensitivity of an electrochemical transducer. The most common strategies for glucose detection are based on using either glucose oxidase or glucose dehydrogenase enzyme.

Electrochemical sensors for glucose, based on the specific glucose oxidizing enzyme glucose oxidase, have generated considerable interest. Several commercial devices based on this principle have been developed and are widely used currently for monitoring of glucose, e.g., self testing by patients at home, as well as testing in physician offices and hospitals. The earliest amperometric glucose biosensors were based on glucose oxidase (GOX) which generates hydrogen peroxide in the presence of oxygen and glucose according to the following reaction scheme:

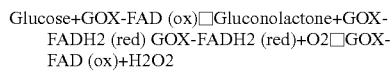

Glucose+GOX-FAD (ox)☐Gluconolactone+GOX-FADH2 (red) GOX-FADH2 (red)+O2☐GOX-FAD (ox)+H2O2

Electrochemical biosensors are used for glucose detection because of their high sensitivity, selectivity and low cost. In principle, amperometric detection is based on measuring either the oxidation or reduction of an electroactive compound at a working electrode (sensor). A constant potential is applied to that working electrode with respect to another electrode used as the reference electrode. The glucose oxidase enzyme is first reduced in the process but is reoxidized again to its active form by the presence of any oxygen resulting in the formation of hydrogen peroxide. Glucose sensors generally have been designed by monitoring either the hydrogen peroxide formation or the oxygen consumption. The hydrogen peroxide produced is easily detected at a potential of +0.6 V relative to a reference electrode such as an Ag/AgCl electrode. However, sensors based on hydrogen peroxide detection are subject to electrochemical interference by the presence of other oxidizable species in clinical samples such as blood or serum. On the other hand, biosensors based on oxygen consumption are affected by the variation of oxygen concentration in ambient air. In order to overcome these drawbacks, different strategies have been developed and adopted.

Selectively permeable membranes or polymer films have been used to suppress or minimize interference from endogenous electroactive species in biological samples. Another strategy to solve these problems is to replace oxygen with electrochemical mediators to reoxidize the enzyme. Mediators are electrochemically active compounds that can reoxidize the enzyme (glucose oxidase) and then be reoxidized at the working electrode as shown below:

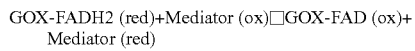

GOX-FADH2 (red)+Mediator (ox)☐GOX-FAD (ox)+Mediator (red)

Organic conducting salts, ferrocene and ferrocene derivatives, ferricyanide, quinones, and viologens are considered good examples of such mediators. Such electrochemical mediators act as redox couples to shuttle electrons between the enzyme and electrode surface. Because mediators can be detected at lower oxidation potentials than that used for the detection of hydrogen peroxide the interference from electroactive species (e.g., ascorbic and uric acids present) in clinical samples such as blood or serum is greatly reduced. For example ferrocene derivatives have oxidation potentials in the +0.1 to 0.4 V range. Conductive organic salts such as tetrathiafulvalene-tetracyanoquinodimethane (TTF-TCNQ) can operate as low as 0.0 Volts relative to a Ag/AgCl reference electrode. Nankai et al, WO 86/07632, published Dec. 31, 1986, discloses an amperometric biosensor system in which a fluid containing glucose is contacted with glucose oxidase and potassium ferricyanide. The glucose is oxidized and the ferricyanide is reduced to ferrocyanide. This reaction is catalyzed by glucose oxidase. After two minutes, an electrical potential is applied, and a current caused by the re-oxidation of the ferrocyanide to ferricyanide is obtained. The current value, obtained a few seconds after the potential is applied, correlates to the concentration of glucose in the fluid.

Figure 3A:
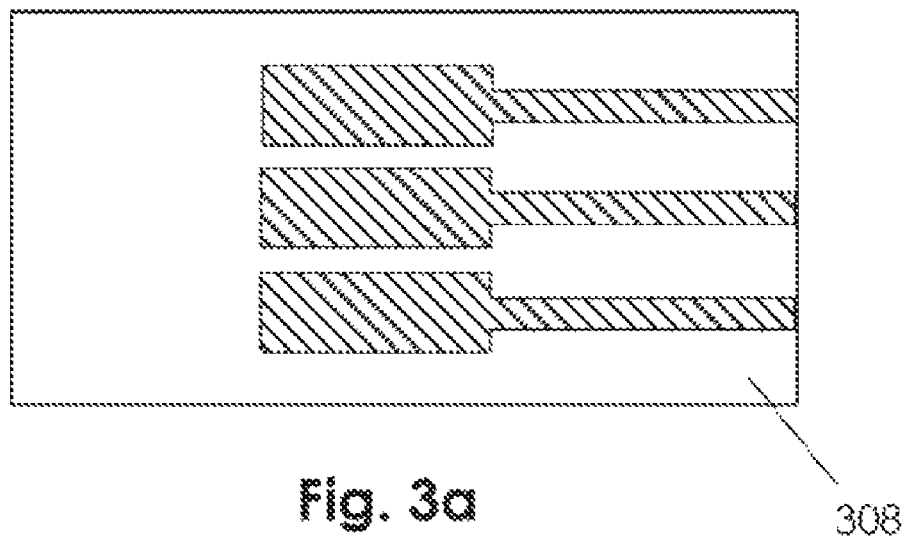
FIGS. 3(a) and (b) are a schematic representative drawing of a three electrode system for use with the glucose sensor of one embodiment of this invention.
Figure 3B:
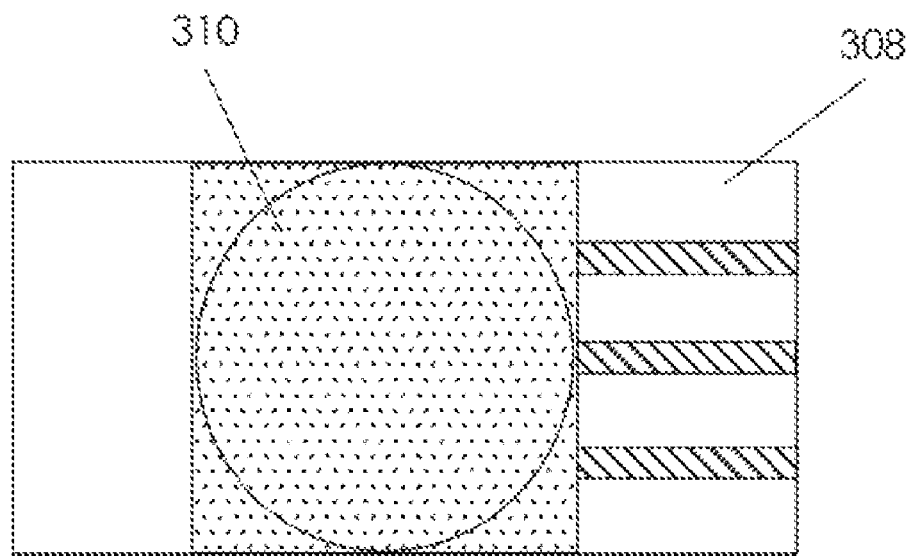

There are multiple glucose sensors that may be used with this invention. In a three electrode system, shown in FIG. 3(a), a working electrode 302 is referenced against a reference electrode 304 (such as Ag/AgCl) and a counter electrode 306 (such as Pt) provides a means for current flow. The three electrodes are mounted on a substrate 308, then covered with a reagent 310, as shown in FIG. 3(b).

Figure 4A:
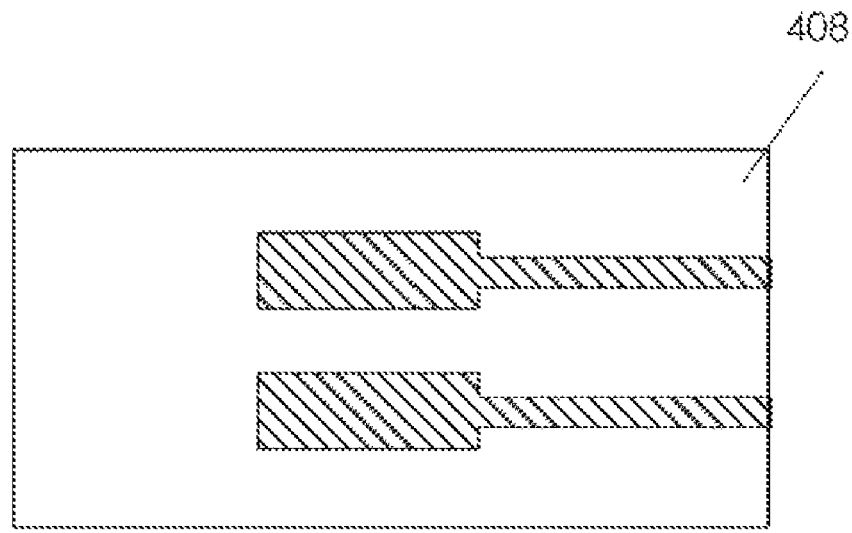
FIGS. 4(a) and (b) are a schematic representative drawing of a two electrode system for use with the glucose sensor of one embodiment of this invention.
Figure 4B:
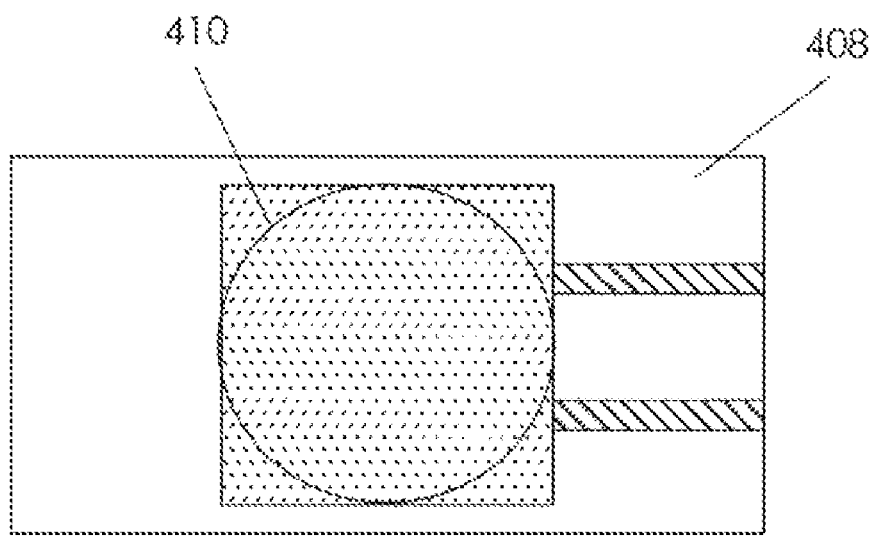

FIG. 4 shows a two electrode system, wherein the working and counter electrodes 402 and 404 are made of different electrically conducting materials. Like the embodiment of FIG. 3, the electrodes 402 and 404 are mounted on a flexible substrate 408 as shown in FIG. 4(a) and covered with a reagent 410, as shown in FIG. 4(b). In an alternative two electrode system, the working and counter electrodes are made of the same electrically conducting materials, where the reagent exposed surface area of the counter electrode is slightly larger than that of the working electrode or where both the working and counter electrodes are substantially of equal dimensions.

In amperometric and coulometric biosensors, immobilization of the enzymes is also very important. Conventional methods of enzyme immobilization include covalent binding, physical adsorption or cross-linking to a suitable matrix may be used.

In some embodiments, the reagent is contained in a reagent well in the biosensor. The reagent includes a redox mediator, an enzyme, and a buffer, and covers substantially equal surface areas of portions of the working and counter electrodes. When a sample containing the analyte to be measured, in this case glucose, comes into contact with the glucose biosensor the analyte is oxidized, and simultaneously the mediator is reduced. After the reaction is complete, an electrical potential difference is applied between the electrodes. In general the amount of oxidized form of the redox mediator at the counter electrode and the applied potential difference must be sufficient to cause diffusion limited electrooxidation of the reduced form of the redox mediator at the surface of the working electrode. After a short time delay, the current produced by the electrooxidation of the reduced form of the redox mediator is measured and correlated to the amount of the analyte concentration in the sample. In some cases, the analyte sought to be measured may be reduced and the redox mediator may be oxidized.

In the present invention, these requirements are satisfied by employing a readily reversible redox mediator and using a reagent with the oxidized form of the redox mediator in an amount sufficient to insure that the diffusion current produced is limited by the oxidation of the reduced form of the redox mediator at the working electrode surface. For current produced during electrooxidation to be limited by the oxidation of the reduced form of the redox mediator at the working electrode surface, the amount of the oxidized form of the redox mediator at the surface of the counter electrode must always exceed the amount of the reduced form of the redox mediator at the surface of the working electrode. Importantly, when the reagent includes an excess of the oxidized form of the redox mediator, as described below, the working and counter electrodes may be substantially the same size or unequal size as well as made of the same or different electrically conducting material or different conducting materials. From a cost perspective the ability to utilize electrodes that are fabricated from substantially the same material represents an important advantage for inexpensive biosensors.

As explained above, the redox mediator must be readily reversible, and the oxidized form of the redox mediator must be of sufficient type to receive at least one electron from the reaction involving enzyme, analyte, and oxidized form of the redox mediator. For example, when glucose is the analyte to be measured and glucose oxidase is the enzyme, ferricyanide or quinone may be the oxidized form of the redox mediator. Other examples of enzymes and redox mediators (oxidized form) that may be used in measuring particular analytes by the present invention are ferrocene and or ferrocene derivative, ferricyanide, and viologens. Buffers may be used to provide a preferred pH range from about 4 to 8. The most preferred pH range is from about 6 to 7. The most preferred buffer is phosphate (e.g., potassium phosphate) from about 0.1 M to 0.5M and preferably about 0.4M. (These concentration ranges refer to the reagent composition before it is dried onto the electrode surfaces.) More details regarding glucose sensor chemistry and operation may be found in: Clark L C, and Lyons C, "Electrode Systems for Continuous Monitoring in Cardiovascular Surgery," Ann NY Acad Sci, 102:29, 1962; Updike S J, and Hicks G P, "The Enzyme Electrode," Nature, 214:986, 1967; Cass, A. E. G., G. Davis. G. D. Francis, et. al. 1984. Ferrocene-mediated enzyme electrode for amperometric determination of glucose. Anal. Chem. 56:667-671; and Boutelle, M. G., C. Stanford. M. Fillenz, et. al. 1986. An amperometric enzyme electrode for monitoring brain glucose in the freely moving rat. Neurosci lett. 72:283-288.

Figure 5:
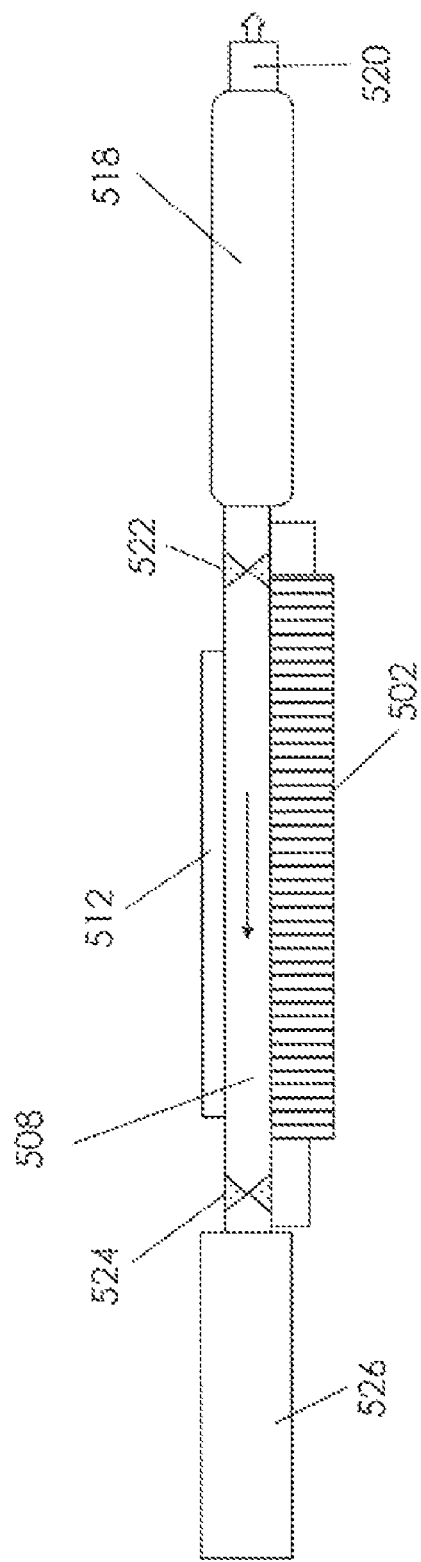
FIG. 5 is a cross-sectional schematic view of a portion of a glucose monitoring device according to yet another embodiment of the invention.

Another embodiment of the disposable portion of the glucose monitor invention is shown in FIG. 5 with a microneedle array 502 and a glucose sensor 512 in fluid communication with a sensing area in channel 508. In this embodiment, actuator 520 is on the side of sensing fluid reservoir 518, and the waste reservoir 526 is expandable. Operation of actuator 520 sends sensing fluid from reservoir 518 through one way flap valve 522 into the sensing area in channel 508 and forces sensing fluid within channel 508 through flap valve 524 into the expandable waste reservoir 526.

In the embodiment of FIG. 5 (and potentially other embodiments), the starting amount of sensing fluid in the calibration reservoir 518 is about 1.0 ml or less, and operation of the sensing fluid actuator 520 sends a few microliters (e.g., 10 μL) of sensing fluid into channel 508. Recalibrating the device three times a day for seven days will use less than 250 μL of sensing fluid.

Figure 6:
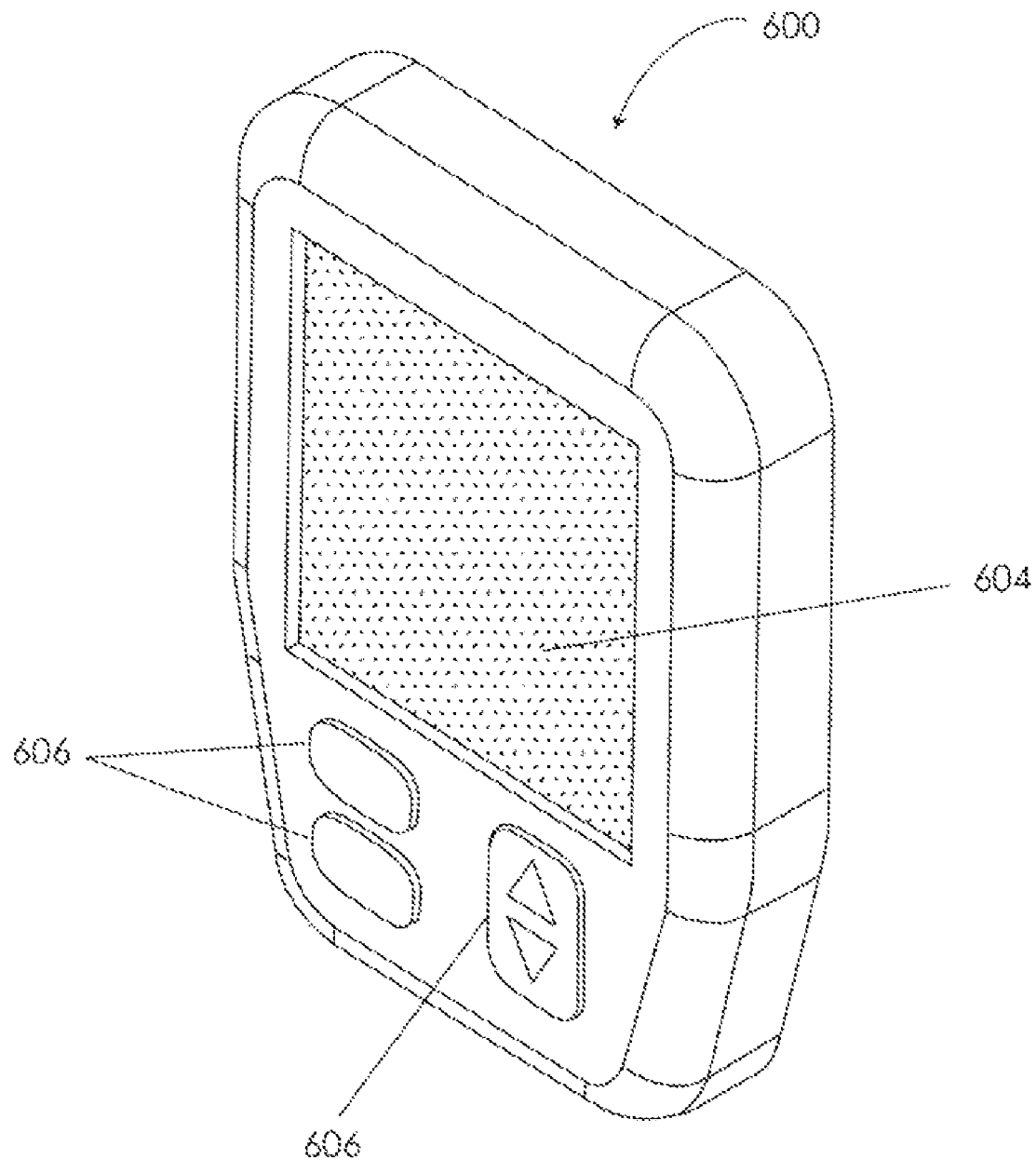
FIG. 6 shows a remote receiver for use with a glucose monitoring system according to yet another embodiment of the invention.
Figure 7:
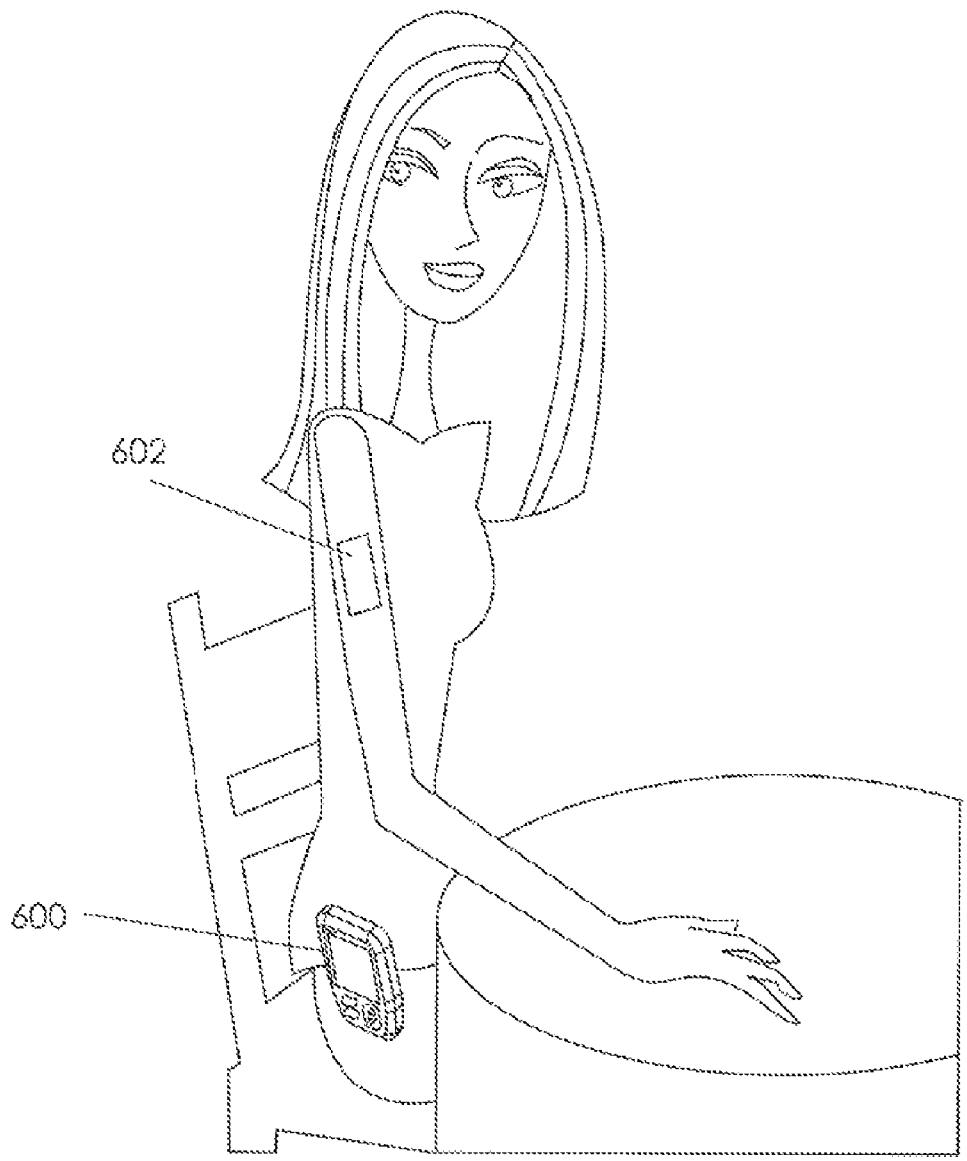
FIG. 7 shows a glucose sensor in place on a user's skin and a remote monitor for use with the sensor.

FIGS. 6 and 7 show a remote receiver for use with a glucose monitoring system. The wireless receiver can be configured to be worn by a patient on a belt, or carried in a pocket or purse. In this embodiment, glucose sensor information is transmitted by the glucose sensor 602 applied to the user's skin to receiver 600 using, e.g., wireless communication such as radio frequency (RF) or Bluetooth wireless. The receiver may maintain a continuous link with the sensor, or it may periodically receive information from the sensor. The sensor and its receiver may be synchronized using RFID technology or other unique identifiers. Receiver 600 may be provided with a display 604 and user controls 606. The display may show, e.g., glucose values, directional glucose trend arrows and rates of change of glucose concentration. The receiver can also be configured with a speaker adapted to deliver an audible alarm, such as high and low glucose alarms. Additionally, the receiver can include a memory device, such as a chip, that is capable of storing glucose data for analysis by the user or by a health care provider.

In some embodiments, the source reservoir for the calibration and sensing fluid may be in a blister pack which maintains its integrity until punctured or broken. The actuator may be a small syringe or pump. Use of the actuator for recalibration of the sensor may be performed manually by the user or may be performed automatically by the device if programmed accordingly. There may also be a spring or other loading mechanism within the reusable housing that can be activated to push the disposable portion—and specifically the microneedles—downward into the user's skin.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of in vivo monitoring of an individual's interstitial fluid comprising:
    creating a plurality of fluid paths through a stratum corneum area of the individual's skin, the fluid paths each comprising a distal end in fluid communication with interstitial fluid of the individual, a proximal end in analyte communication with a sensing area located outside of the patient's body, and an interior space extending between the distal and proximal ends of the fluid path;
    moving sensing fluid out of a sensing fluid reservoir and into the sensing area;
    holding the sensing fluid in the sensing area in a non-flowing manner;
    allowing at least one analyte to passively diffuse from the patient's interstitial fluid through the fluid paths and into the sensing area;
    sensing a concentration of the at least one analyte in the sensing fluid using a sensor located at least partially in the sensing area during the holding step.

2. The method of claim 1 wherein fluid in the fluid paths is not moving when the at least one analyte is passively diffusing there-through.

3. The method of claim 1 wherein there is no fluid movement between the distal ends of the fluid paths and the sensor when the at least one analyte is passively diffusing through the fluid paths and into the sensing area.

4. The method of claim 1 wherein no interstitial fluid is extracted from the individual during the diffusion and sensing steps.

5. The method of claim 1 further comprising displaying analyte concentration information remote from the stratum corneum area of the individual's skin.

6. The method of claim 5 further comprising wirelessly communicating analyte concentration information to a display.

7. The method of claim 1 wherein the sensing step is performed by a sensor in fluid communication with the sensing area and the interior spaces of the fluid paths, the method further comprising calibrating the sensor by moving sensing fluid into the sensing area.

8. The method of claim 7 further comprising moving sensing fluid out of the sensing area as sensing fluid is moved into the sensing area.

9. The method of claim 1 further comprising attaching a device comprising the sensor area and the sensor to the individual with adhesive.

10. The method of claim 1 further comprising providing a membrane located between the distal ends of the fluid paths and the sensor.

11. The method of claim 1 wherein creating the plurality of fluid paths through the stratum corneum area of the individual's skin comprises applying a microneedle array to the stratum corneum area.

12. The method of claim 1 wherein the proximal ends of the fluid paths are in fluid communication with the sensing area.

13. The method of claim 1 wherein the step of moving sensing fluid comprises operating an actuator.

14. The method of claim 1 wherein the step of moving sensing fluid comprises moving sensing fluid having a glucose concentration of between about 0 mg/dl and about 400 mg/dl.

15. The method of claim 1 wherein the sensing fluid reservoir, sensing area, and at least part of the sensor being supported by a first part of a housing, the method further comprising attaching the first part of the housing to a second part of the housing prior to the moving sensing fluid step, the second part of the housing comprising an electrical connection to the at least part of the sensor in the first part of the housing.

16. The method of claim 15 further comprising separating the second part of the housing from the first part of the housing after the sensing step.

* * * * *